US00PP16423P2

(12) United States Plant Patent
Venecourt

(10) Patent No.: US PP16,423 P2
(45) Date of Patent: Apr. 11, 2006

(54) ***ORNITHOGALUM* PLANT NAMED 'NAMIB GOLD'**

(50) Latin Name: *Ornithogalum Conicum×dubium*
Varietal Denomination: Namib Gold

(75) Inventor: Gail Margaret Littlejohn Venecourt, Elsenburg (ZA)

(73) Assignee: ARC Fynbos, Elsenburg (ZA)

( * ) Notice: Subject to any disclaimer, the term of this patent is extended or adjusted under 35 U.S.C. 154(b) by 250 days.

(21) Appl. No.: 10/903,573

(22) Filed: Jul. 30, 2004

(51) Int. Cl.
*A01H 5/00* (2006.01)

(52) U.S. Cl. ..... Plt./263
(58) Field of Classification Search ..... Plt./263
See application file for complete search history.

(56) References Cited

U.S. PATENT DOCUMENTS

PP12,085 P2 * 9/2001 Littlejohn et al. ..... Plt./263
PP12,184 P2 * 11/2001 Littlejohn et al. ..... Plt./263

OTHER PUBLICATIONS

UPOV ROM GTITM Computer Database, GTI Jouve Retrieval Software 2004/06 Citations for 'Namib Gold'.*

* cited by examiner

*Primary Examiner*—Kent Bell
*Assistant Examiner*—W. C. Haas
(74) *Attorney, Agent, or Firm*—Mark P. Bourgeois

(57) ABSTRACT

A new cultivar of *Ornithogalum* plant named 'Namib Gold' that is characterized by a long stem, yellow flowers and vigorous growth. In combination, these traits set 'Namib Gold' apart from other known existing varieties of *Ornithogalum*.

1 Drawing Sheet

Botanical designation: *Ornithogalum conicum×O. dubium.*
Variety denomination: 'Namib Gold'.

BACKGROUND OF THE INVENTION

The present invention relates to a new and distinct cultivar of *Ornithogalum* plant botanically known as *Ornithogalum* and hereinafter referred to by the cultivar name 'Namib Gold'.

The new cultivar is the product of a breeding program conducted by the inventor in a cultivated area of Elsenburg, South Africa. The objective of the breeding program is to develop *Ornithogalum* cultivars that are tall with yellow flowers and that are vigorous.

'Namib Gold' is a hybrid that originated from the crossing of the female or seed parent an unnamed *Ornithogalum conicum* (not patented) and the male or pollen parent an unnamed *Ornithogalum dubium* (not patented). The cultivar 'Namib Gold' was selected by the inventor in 1999 as a single plant within the progeny of the stated cross in Elsenburg, South Africa.

Asexual reproduction by tissue culture micropropagation of the new cultivar 'Namib Gold' was first taken in 2000 in Groot Drakenstein, South Africa. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Ornithogalum* cultivar 'Namib Gold'. These traits in combination distinguish 'Namib Gold' as a new and distinct cultivar apart from all other existing varieties of *Ornithogalum* known to the inventor.

1. *Ornithogalum* 'Namib Gold' exhibits a long stem.
2. *Ornithogalum* 'Namib Gold' exhibits yellow flowers.
3. *Ornithogalum* 'Namib Gold' exhibits vigorous growth.

The closest comparison varieties are *Ornithogalum* 'Namib Sun'(U.S. Plant Pat. No. 12,184) and *Ornithogalum* 'Namib Sunshine' (unpatented). 'Namib Gold' has darker yellow flowers than 'Namib Sun'. 'Namib Gold' has a longer stem than 'Namib Sun'. 'Namib Gold' has a longer stem than 'Namib Sunshine'.

The new cultivar 'Namib Gold' is distinguishable from the female parent, an unnamed *Ornithogalum conicum,* by the following characteristics:

1. 'Namib Gold' has yellow flowers, the female parent has white flowers.

The new cultivar 'Namib Gold' is distinguishable from the male parent, an unnamed *Ornithogalum dubium,* by the following characteristics:

1. 'Namib Gold' has a longer stem length.

BRIEF DESCRIPTION OF THE DRAWING

The accompanying photograph illustrates the distinguishing traits of *Ornithogalum* 'Namib Gold'. The drawing shows a close up of the flowers and stem of the claimed plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Ornithogalum* cultivar named 'Namib Gold'. Data was collected in Hillegom, The Netherlands from 18 month old fieldgrown plants from Elsenburg, South Africa. greenhouse grown plants in 1.0 liter containers. The time of year was Winter and the average temperature was 18° Centigrade during the Summer and 4° Centigrade during the Winter. The light level was natural outdoor light and there were no photoperiodic treatments or growth retardants used. Color determinations are in accordance with The Royal Horticultural Society Colour Chart 2001 edition, except where general color terms of ordinary dictionary significance are used. The growing requirements are similar to the species. 'Namib Gold' has not been tested under all possible conditions and phenotypic differences may be observed with variations in environmental, climatic, and cultural conditions, however, without any variance in genotype.

Botanical classification: *Ornithogalum conicum*×*O. dubium* 'Namib Gold'.
Plant type: Herbaceous perennial.
Parentage:
*Female parent.*—An unnamed *Ornithogalum conicum.*
*Male parent.*—An unnamed *Ornithogalum dubium.*
Vigor: Moderate to High.
Growth habit: Upright.
Plant shape: Bulbous with basal leaves and inflorescences on upright stems.
Suitable container size: Fieldgrown.
Height: Average 81 cm. in height.
Width: Average 26 cm. in width.
Hardiness: USDA Zone 8.
Propagation: Cuttings or tissue culture.
Time to initiate roots: Approximately 30 days to produce roots on an initial cutting.
Time to produce a rooted cutting or liner: Approximately 60 days.
Crop time: 2 years from tissue culture to a finished plant.
Bulb:
*Bulb shape.*—Ovate.
*Bulb dimensions.*—Average 2.5 cm. in length, 2.2 cm. in diameter.
*Bulb color.*—159C to 159D.
Stem:
*Branching habit.*—Leaves grow directly from bulb.
*Pinching.*—None needed.
*Stem color.*—141A toward bottom, 143A to 143B near top.
*Pubescence.*—Absent.
*Internode length.*—Average 1 mm. between nodes.
*Shape.*—Rounded.
*Surface.*—Dull, smooth.
*Stem strength.*—Moderate.
Foliage:
*Texture.*—Smooth, relatively thick and slightly leathery, moderately glossy.
*Leaf arrangement.*—Crowded at the base.
*Compound or single.*—Single.
*Quantity of leaves per lateral branch.*—8.
*Leaf shape.*—Ligulate.
*Leaf apex.*—Acute.
*Leaf base.*—Sheath.
*Leaf length.*—Average 35.5 cm. in length.
*Leaf width.*—Average 3.5 cm. in width.
*Pubescence.*—None.
*Leaf margin.*—Entire.
*Vein pattern.*—Parallel.
*Young leaf color* (*upper surface*).—144A, base 145B to 145C.
*Young leaf color* (*lower surface*).—144A, base 145B to 145C.
*Mature leaf color* (*upper surface*).—144A to 146A, base 145B to 145C.
*Mature leaf color* (*lower surface*).—146A to 146B, base 145A to 145B.
*Vein color* (*upper and lower surfaces*).—Same as leaf surface, varies from 144A to 145A to 145B to 145C to 146A to 146B to 146C to match the leaf coloration proximate to the vein.
*Leaf attachment.*—Sessile.
*Durability of foliage to stress.*—Moderate.
Flower:
*Flower arrangement.*—Terminal racemes on long peduncles.
*Inflorescence type.*—Raceme.
*Inflorescence dimensions.*—Average 7.1 cm. in diameter and 15 cm. in height.
*Quantity of flowers and buds per plant.*—Approximately 45.
*Flowering season.*—Early spring.
*Rate of flower opening.*—15% of the flowers are opened at once.
*Fragrance.*—None.
*Self-cleaning or persistent.*—Persistent.
*Flower bud length.*—Average 1.1 cm. in length.
*Flower bud diameter.*—Average 7 mm. in diameter.
*Flower bud shape.*—Ovate.
*Bud color.*—150B.
*Rate of bud opening.*—3 days.
*Flower aspect.*—Upright to outward.
*Flower shape.*—Rotate.
*Flower dimensions.*—Average 3.9 cm. in diameter and 1.1 cm. in height.
*Flower longevity.*—Inflorescence lasts approximately 6 to 7 weeks.
*Longevity as a cut flower.*—Approximately 3 weeks.
*Tepal appearance.*—Dull.
*Tepal texture.*—Glabrous.
*Tepal arrangement.*—Rotate.
*Number of tepals.*—6 in number.
*Tepals fused or unfused.*—Unfused.
*Tepal shape.*—Obovate.
*Tepal margin.*—Entire.
*Tepal apex.*—Obtuse to abruptly acute.
*Tepal dimensions.*—Average 1.8 cm. in length and 1 cm. in width.
*Tepal color when opening* (*upper side*).—8B, base 153A to 153B.
*Tepal color when opening* (*under side*).—8B, base 153C to 153D.
*Tepal color when fully opened* (*upper side*).—8B to 8C, base 8A.
*Tepal color when fully opened* (*under side*).—8B to 8C, base 153D.
*Tepal color fading to.*—Not fading.
Calyx:
*Calyx shape.*—Rotate.
*Calyx dimensions.*—Average 1.1 cm. in length and 3.9 cm. in width.
Peduncle:
*Peduncle dimensions.*—Average 67 cm. in length and 8 mm. in diameter.
*Peduncle angle with soil plane.*—90°.
*Peduncle color.*—141A to 143A to 143B near the top.
*Peduncle strength.*—Moderate.

Bracts:

*Number of bracts.*—1 in number.

*Bract dimensions.*—Average 4.1 cm. in length and 1.8 cm. in width.

*Bract shape.*—Lanceolate.

*Bract apex.*—Long apiculate.

*Bract base.*—Broad Cuneate.

*Bract color* (*upper side*).—143A to 143B.

*Bract color* (*under side*).—143A.

Pedicels:

*Pedicel dimensions.*—Average 4.6 cm. in length and 2 mm. in diameter.

*Pedicel angle.*—65°.

*Pedicel color.*—143A, base 144A.

*Pedicel strength.*—Strong.

Reproduction organs:

*Stamen number.*—6.

*Anther shape.*—Linear, with longitudinal splits.

*Anther dimensions.*—Average 3 mm. in length, 1 mm. in diameter.

*Anther color.*—156C to 156D.

*Amount of pollen.*—Very low.

*Pollen color.*—17C.

*Pistil number.*—1 in number.

*Pistil dimensions.*—Average 3.5 mm. in length.

*Stigma shape.*—Split in three segments.

*Stigma color.*—160A.

*Style length.*—Average 2 mm.

*Style color.*—153C.

*Ovary color.*—152A to 152B.

Seed: Seed production has not been observed.

Disease resistance: Plants of the new *Ornithogalum* have not been observed for disease resistance.

It is claimed:

1. A new and distinct variety of *Ornithogalum* plant named 'Namib Gold' as described and illustrated.

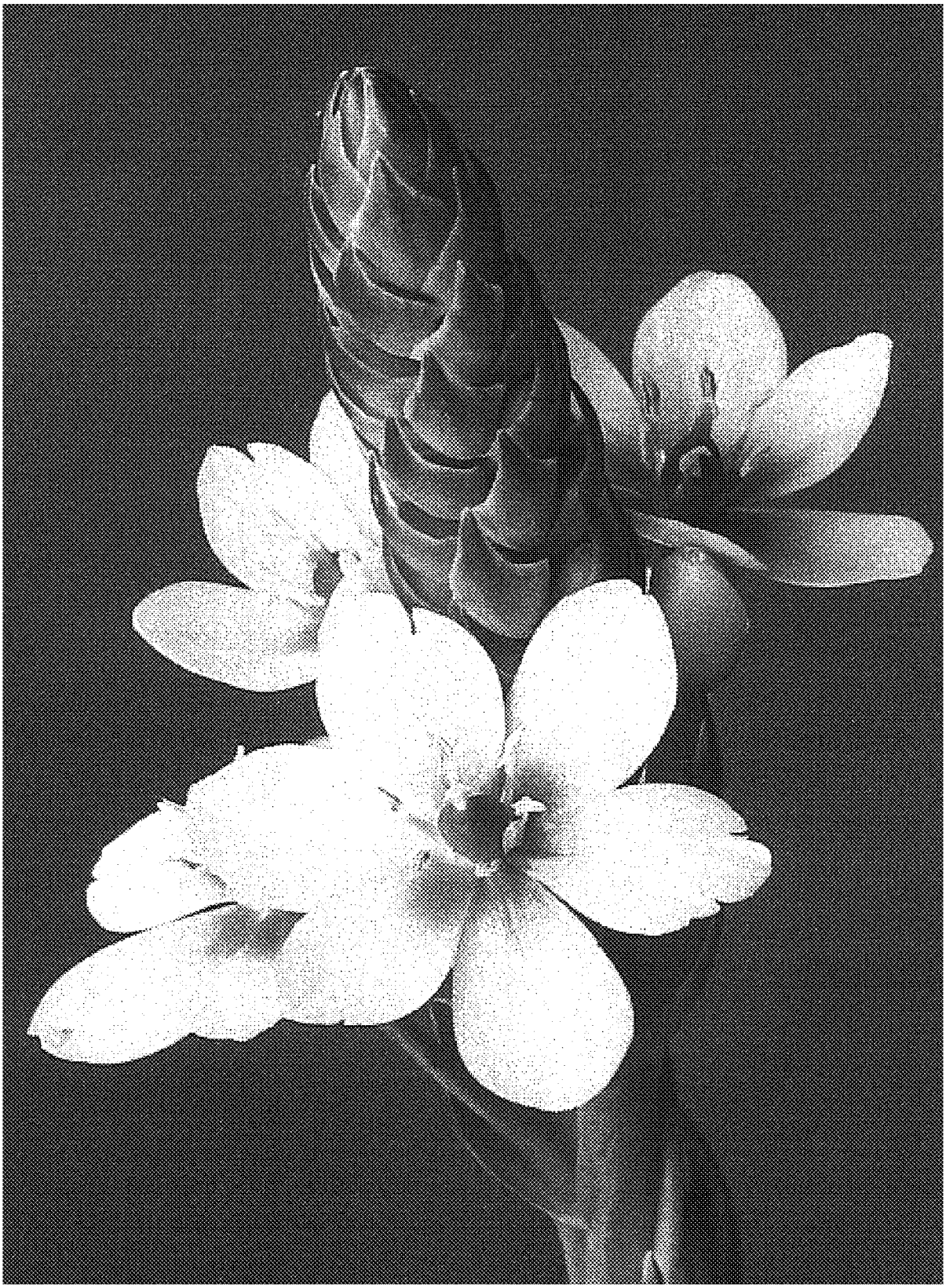

* * * * *